(12) United States Patent
Bosworth et al.

(10) Patent No.: US 12,053,172 B2
(45) Date of Patent: Aug. 6, 2024

(54) SUTURE PASSER DEVICE

(71) Applicant: Conmed Corporation, Utica, NY (US)

(72) Inventors: Adrian Bosworth, Bradenton, FL (US); James Hutter, Largo, FL (US); Robert Thibodeau, Saint Petersburg, FL (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 16/772,610

(22) PCT Filed: Dec. 14, 2018

(86) PCT No.: PCT/US2018/065669
§ 371 (c)(1),
(2) Date: Jun. 12, 2020

(87) PCT Pub. No.: WO2019/118835
PCT Pub. Date: Jun. 20, 2019

(65) Prior Publication Data
US 2020/0390435 A1 Dec. 17, 2020

Related U.S. Application Data

(60) Provisional application No. 62/598,545, filed on Dec. 14, 2017.

(51) Int. Cl.
*A61B 17/04* (2006.01)
*A61B 17/00* (2006.01)
*A61B 17/06* (2006.01)

(52) U.S. Cl.
CPC .... *A61B 17/0469* (2013.01); *A61B 17/06109* (2013.01); *A61B 2017/00367* (2013.01); *A61B 2017/047* (2013.01)

(58) Field of Classification Search
CPC .... A61B 2017/047; A61B 2017/00367; A61B 17/06109; A61B 17/0469
(Continued)

(56) References Cited

U.S. PATENT DOCUMENTS 2,579,192 A * 12/1951 Kohl ................. A61B 17/0469
112/169
5,387,221 A * 2/1995 Bisgaard ............ A61B 17/0469
606/147

(Continued)

OTHER PUBLICATIONS

International Search Report Form PCT/ISA/220, International Application No. PCT/US2018/065669, pp. 1-15, Dated Mar. 19, 2019.
(Continued)

*Primary Examiner* — Kankindi Rwego
(74) *Attorney, Agent, or Firm* — Bond, Schoeneck & King, PLLC; Frederick J. M. Price

(57) ABSTRACT

A suture passer device for passing a length of suture through an object. The suture passer device includes a hollow tube having a proximal end and a curved distal tube portion extending to a distal end. The suture passer device also includes a handle attached to the proximal end of the hollow tube, an actuator on the handle movable between first, second, and third positions, and an internal arm within the curved distal tube portion and connected to the actuator. The internal arm is movable between first, second, and third configurations. When the actuator is in the first position, the internal arm extends out from the distal tube portion at an angle from the distal tube portion in the first configuration. When the actuator is in the second position, the internal arm is retracted within the distal tube portion in the second configuration.

5 Claims, 12 Drawing Sheets

(58) Field of Classification Search
USPC .................................................. 606/145, 144
See application file for complete search history.

(56) References Cited

U.S. PATENT DOCUMENTS

| | | | |
|---|---|---|---|
| 5,499,991 A * | 3/1996 | Garman | A61B 17/0483 |
| | | | 606/148 |
| 5,817,111 A * | 10/1998 | Riza | A61B 17/06109 |
| | | | 606/148 |
| 5,954,733 A | 9/1999 | Yoon | |
| 6,022,360 A | 2/2000 | Reimels et al. | |
| 6,099,550 A | 8/2000 | Yoon | |
| 6,517,552 B1 | 2/2003 | Nord et al. | |
| 6,616,674 B2 | 9/2003 | Schmieding | |
| 6,629,984 B1 | 10/2003 | Chan | |
| 6,716,224 B2 | 4/2004 | Singhatat | |
| 6,770,084 B1 | 8/2004 | Bain et al. | |
| 6,896,686 B2 | 5/2005 | Weber et al. | |
| 6,932,826 B2 | 8/2005 | Chan | |
| 7,108,700 B2 | 9/2006 | Chan | |
| 7,118,583 B2 | 10/2006 | O'Quinn et al. | |
| 7,169,156 B2 | 1/2007 | Hart | |
| 7,220,266 B2 | 5/2007 | Gambale | |
| 7,704,262 B2 | 4/2010 | Bellafiore et al. | |
| 7,749,237 B2 | 7/2010 | Chan | |
| 7,842,050 B2 | 11/2010 | Diduch et al. | |
| 7,879,048 B2 | 2/2011 | Bain et al. | |
| 7,883,519 B2 | 2/2011 | Oren et al. | |
| 7,951,157 B2 | 5/2011 | Gambale | |
| 7,972,344 B2 | 7/2011 | Murray et al. | |
| 8,066,718 B2 | 11/2011 | Weisel et al. | |
| 8,157,816 B2 | 4/2012 | Rotella et al. | |
| 8,328,824 B2 | 12/2012 | Hart | |
| 8,333,774 B2 | 12/2012 | Morrison | |
| 8,382,772 B2 | 2/2013 | Rotella et al. | |
| 8,469,974 B2 | 6/2013 | Skinlo et al. | |
| 8,500,757 B2 | 8/2013 | Miraki et al. | |
| 8,562,629 B2 | 10/2013 | Bain et al. | |
| 8,568,428 B2 | 10/2013 | Mcclurg et al. | |
| 8,585,714 B2 | 11/2013 | Weisel et al. | |
| 8,591,527 B2 | 11/2013 | Fan et al. | |
| 8,623,032 B2 | 1/2014 | Diduch et al. | |
| 8,663,251 B2 | 3/2014 | Burkhart et al. | |
| 8,758,368 B2 | 6/2014 | Weisel et al. | |
| 8,808,313 B2 | 8/2014 | Thorne et al. | |
| 8,814,886 B2 | 8/2014 | Berberich et al. | |
| 8,888,795 B2 | 11/2014 | Chu | |
| 8,992,570 B2 | 3/2015 | Gambale et al. | |
| 9,039,721 B2 | 5/2015 | Ziniti et al. | |
| 9,089,321 B2 | 7/2015 | Snyder et al. | |
| 9,089,322 B2 | 7/2015 | Spenciner et al. | |
| 9,101,355 B2 | 8/2015 | Lantz et al. | |
| 9,101,356 B1 | 8/2015 | Jordan | |
| 9,149,268 B2 | 10/2015 | Graul et al. | |
| 9,179,905 B2 | 11/2015 | Pamichev et al. | |
| 9,192,375 B2 | 11/2015 | Skinlo et al. | |
| 9,198,655 B2 | 12/2015 | Skinlo et al. | |
| 9,247,935 B2 | 2/2016 | George et al. | |
| 9,271,719 B2 | 3/2016 | Skinlo et al. | |
| 9,271,720 B2 | 3/2016 | Stone et al. | |
| 9,332,980 B2 | 5/2016 | George et al. | |
| 9,351,721 B2 | 5/2016 | Auerbach et al. | |
| 9,358,001 B2 | 6/2016 | Fan et al. | |
| 9,364,214 B2 | 6/2016 | Courage | |
| 9,451,943 B2 | 9/2016 | Pamichev et al. | |
| 9,451,951 B2 | 9/2016 | Sullivan et al. | |
| 9,451,953 B2 | 9/2016 | Sengun | |
| 9,572,566 B2 | 2/2017 | Skinlo et al. | |
| 9,801,622 B2 | 10/2017 | Weisel et al. | |
| 9,801,624 B2 | 10/2017 | Melsheimer et al. | |
| 9,808,240 B2 | 11/2017 | Parsons et al. | |
| 9,826,973 B2 | 11/2017 | Graul et al. | |
| 9,877,716 B2 | 1/2018 | Snyder et al. | |
| 9,888,915 B2 | 2/2018 | Torrie | |
| 9,931,114 B2 | 4/2018 | Stewart et al. | |
| 9,936,941 B2 | 4/2018 | Weisel et al. | |
| 9,936,946 B2 | 4/2018 | Haines et al. | |
| 10,058,319 B2 | 8/2018 | Konrath et al. | |
| 10,092,285 B2 | 10/2018 | Graul et al. | |
| 10,092,287 B2 | 10/2018 | Oren et al. | |
| 10,098,631 B2 | 10/2018 | Stewart et al. | |
| 10,123,793 B2 | 11/2018 | Pamichev et al. | |
| 10,123,794 B2 | 11/2018 | Flom et al. | |
| 10,136,884 B2 | 11/2018 | Graul et al. | |
| 10,143,464 B2 | 12/2018 | George et al. | |
| 10,231,730 B2 | 3/2019 | Heneveld | |
| 10,238,379 B2 | 3/2019 | Graul et al. | |
| 10,265,062 B2 | 4/2019 | Foerster et al. | |
| 10,299,786 B2 | 5/2019 | Levine et al. | |
| 10,357,243 B2 | 7/2019 | Skinlo et al. | |
| 10,363,025 B2 | 7/2019 | Antz et al. | |
| 10,405,850 B2 | 9/2019 | Stewart et al. | |
| 10,426,456 B2 | 10/2019 | Pamichev et al. | |
| 10,441,271 B2 | 10/2019 | Oren et al. | |
| 10,441,276 B2 | 10/2019 | Sanders et al. | |
| 10,485,532 B2 | 11/2019 | Norton et al. | |
| 10,555,731 B2 | 2/2020 | Weisel et al. | |
| 10,667,805 B1 | 6/2020 | Bourland, III et al. | |
| 10,682,133 B2 | 6/2020 | Torrie | |
| 10,743,861 B2 | 8/2020 | Weisel et al. | |
| 10,765,420 B2 | 9/2020 | Lunn et al. | |
| 10,828,023 B2 | 11/2020 | Stewart et al. | |
| 10,905,410 B2 | 2/2021 | Diduch et al. | |
| 2004/0087978 A1 | 5/2004 | Velez et al. | |
| 2005/0021055 A1 | 1/2005 | Toubia et al. | |
| 2006/0074438 A1 | 4/2006 | Chan | |
| 2007/0118152 A1 | 5/2007 | Page | |
| 2009/0082787 A1 | 3/2009 | Pang | |
| 2010/0198235 A1 | 8/2010 | Pierce et al. | |
| 2010/0324575 A1 | 12/2010 | Chan | |
| 2012/0123448 A1 * | 5/2012 | Flom | A61B 17/0483 |
| | | | 606/144 |
| 2012/0143220 A1 | 6/2012 | Morgan et al. | |
| 2013/0165954 A1 | 6/2013 | Dreyfuss et al. | |
| 2013/0274768 A1 | 10/2013 | Skinlo et al. | |
| 2014/0207188 A1 | 7/2014 | Yearsley et al. | |
| 2014/0222033 A1 | 8/2014 | Foerster et al. | |
| 2015/0094739 A1 | 4/2015 | Norton et al. | |
| 2017/0020510 A1 | 1/2017 | Skinlo et al. | |
| 2017/0042533 A1 | 2/2017 | Lunn et al. | |
| 2017/0181737 A1 | 6/2017 | Sanders et al. | |
| 2017/0215876 A1 | 8/2017 | Norton et al. | |
| 2017/0325809 A1 | 11/2017 | Stewart et al. | |
| 2019/0159772 A1 | 5/2019 | Norton et al. | |
| 2020/0046341 A1 | 2/2020 | Skinlo et al. | |
| 2020/0405488 A1 | 12/2020 | Pettus, IV et al. | |
| 2021/0052268 A1 | 2/2021 | Weisel et al. | |

OTHER PUBLICATIONS

Stryker Australia and New Zealand Sports Medicine Product Guide 2nd Edition, www.strykermed.com, pp. 1-56, dated 2015.
Smith and Nephew Accu-Pass Suture Shuttle Brochure, www.smith-nephew.com, pp. 1-2, dated Dec. 2007.
1 KR Office Action, App No. 10-2020-7020028, dated Jun. 17, 2022, pp. 3-9.

\* cited by examiner

SUTURE PASSER DEVICE

CROSS-REFERENCES TO RELATED APPLICATIONS

This application is a national stage application under 35 U.S.C. 371 based on international patent application PCT/US18/65669 filed on Dec. 14, 2018, which claims priority to U.S. Provisional Patent Application Ser. No. 62/598,545, filed on Dec. 14, 2017.

BACKGROUND OF THE INVENTION

1. Field of the Invention

The present disclosure is directed generally to surgical apparatus and methods and, more particularly, to a surgical apparatus and method for passing suture through tissue.

2. Description of Related Art

It is common in surgical procedures that suture must be passed through tissue. For example, in many orthopedic repair procedures, it is necessary to pass suture through tissue to bring the tissue in apposition with a bone. Generally, suture is attached to or otherwise threaded through a needle and the needle is passed through the tissue. In some procedures, it is difficult to access the tissue at the surgical site. In those instances, a suture passer device is often used to steer or guide the needle through a proximal side of the tissue, to a distal side of the tissue, and back out through the proximal side of the tissue. However, many conventional suture passers do not consistently or sufficiently secure the suture when moving through the tissue. Further, many conventional suture passers leave the needle exposed while passing through the tissue, which may cause additional damage or trauma to the surrounding tissue.

Therefore, a need exists for a new and improved method and apparatus for passing suture through tissue which secures suture and minimizes additional trauma when the needle passes through the tissue.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention recognize that there are potential problems and/or disadvantages with the conventional suture passer devices. For example, conventional suture passers do not consistently or sufficiently secure the suture when moving through the tissue (as described above). Therefore, a need exists for suture passer device which secures suture and minimizes additional trauma when the needle passes through the tissue. Various embodiments of the present invention may be advantageous in that they may solve or reduce one or more of the potential problems and/or disadvantages discussed herein.

The present disclosure is directed to an inventive configuration, structure, and resulting function of a suture passer device and a method for passing a length of suture through an object. According to an aspect, the suture passer device includes a hollow tube having a proximal end and a curved distal tube portion extending to a distal end. The suture passer device also includes a handle attached to the proximal end of the hollow tube, an actuator on the handle movable between a first position, second position, and third position, and an internal arm within the curved distal tube portion and connected to the actuator. The internal arm is movable between a first configuration, second configuration, and third configuration. When the actuator is in the first position, the internal arm extends out from the distal tube portion at an angle from the distal tube portion in the first configuration. When the actuator is in the second position, the internal arm is retracted proximally further within the distal tube portion in the second configuration as compared to the first configuration According to an another aspect, the method for passing a length of suture through an objects includes (but is not limited to) the steps of: (i) providing a suture passer device having a hollow tube with a proximal end and a curved distal tube portion extending to a distal end, a handle attached to the proximal end of the hollow tube, an actuator on the handle movable between a first position and a second position, and an internal arm within the curved distal tube portion and connected to the actuator, the internal arm movable between a first configuration and a second configuration, wherein when the actuator is in the first position, the internal arm extends out from the distal tube portion at an angle from the distal tube portion in the first configuration, and when the actuator is in the second position, the internal arm is retracted proximally further within the distal tube portion in the second configuration as compared to the first configuration; (ii) moving the actuator to the first position; (iii) positioning a length of suture between the internal arm and the distal tube portion; (iv) moving the actuator to the second position; (v) advancing the distal tube portion through a first side of the object to a second side of the object; (vi) releasing the suture from between the internal arm and the distal tube portion on the second side of the object; (vii) moving the actuator to the first position; and (viii) retracting the distal tube portion from the second side of the object to the first side of the object.

Suture material or sutures, as the terms are used and described herein, include monofilament or multi-filament suture as well as any other metallic or non-metallic filamentary or wire-like material suitable for performing the function of a suture. This material can include both bioabsorbable and non-absorbable materials.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
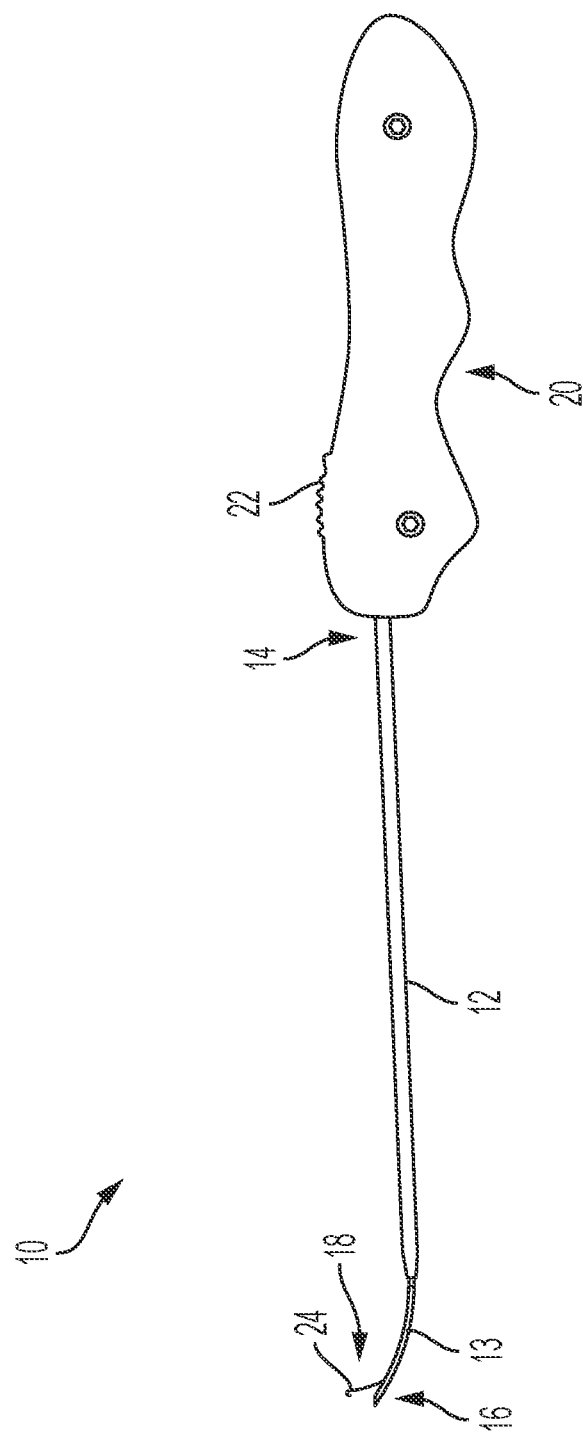
FIG. 1 is a side view schematic representation of a suture passer device, according to an embodiment.
Figure 11:
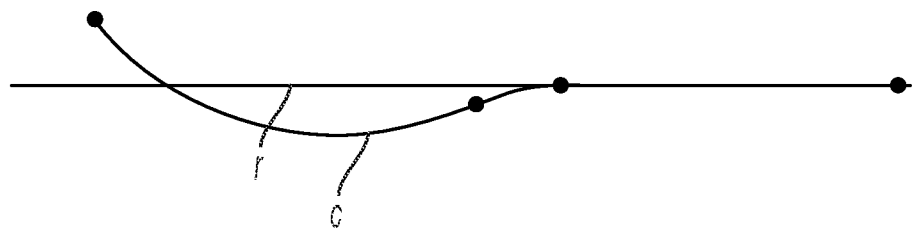
FIG. 11 is a diagrammatic view of the curvature of the curved distal tube portion, according to an embodiment.
Figure 12:
FIG. 12 is a side view schematic representation of the curved distal tube portion, according to an embodiment.

Referring now to the figures, wherein like reference numerals refer to like parts throughout, FIG. 1 shows a side view schematic representation of a suture passer device 10, according to an embodiment. The suture passer device 10 comprises a hollow tube 12 having a proximal end 14, a distal end 16, and an internal arm 18 positioned within the hollow tube 12. In the depicted embodiment, the hollow tube 12 comprises a curved distal tube portion 13 extending from a position between the proximal and distal ends 14, 16 to the distal end 16; however, in other embodiments, the hollow tube 12 may be a straight tube extending from the proximal end 14 to the distal end 16. A curvature c of the curved distal tube portion 13 aids in obtaining proper placement of the curved distal tube portion 13 through a labrum. Various curvatures c of the curved distal tube portion 13 can be used for different procedures. An embodiment of the curvature c of the curved distal tube portion 13 is shown in FIG. 11. The curvature c of the curved distal tube portion 13 has a radius r. In the embodiment shown in FIG. 11, the radius r is 9.2722 mm. As shown in FIG. 12, the curved distal tube portion 13 has an overbite b over the midline m extending centrally through the curved distal tube portion 13. In an embodiment, the overbite b is 4 mm. In other embodiments, the overbite b is within the range of 3-5 mm. Further, the curved distal tube portion 13 can extend in any direction from the hollow tube 12, such as upward (as shown in FIG. 1) or sideways (by rotating the curved distal tube portion 13 in FIG. 1 90 degrees).

Figure 4:
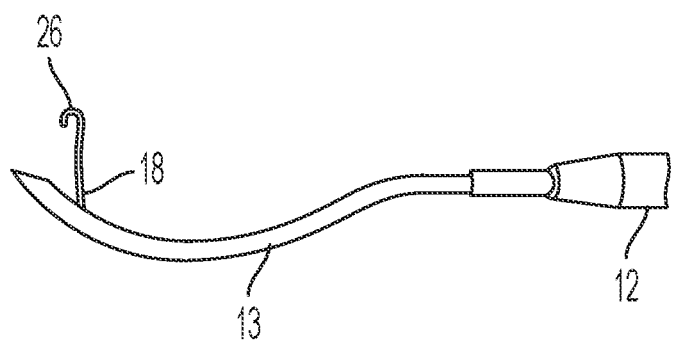
FIG. 4 is a side view schematic representation of a distal tube portion of the suture passer device in the first configuration, according to an embodiment.

The suture passer device 10 also includes a proximal handle 20 attached to the proximal end 14 of the hollow tube 12. A proximal end (not shown) of the internal arm 18 is connected, directly or indirectly, to an actuator 22 attached to the handle 20. In the depicted embodiment, the internal arm 18 comprises a straight distal end 24. In an alternative embodiment, the distal end 24 of the internal arm 18 comprises a hook 26 (FIG. 4). The distal end 24 (or hook 26) is configured to extend through and retract from the open, distal end 16 of the curved distal tube portion 13. Movement of the internal arm 18, including the distal end 16 (or hook 26), is controlled by movement of the actuator 22. In an embodiment, the actuator 22 is movable between a first position, a second position, and a third position, while the distal end 16 (or hook 26) is movable between a first configuration, a second configuration, and a third configuration.

Figure 2:
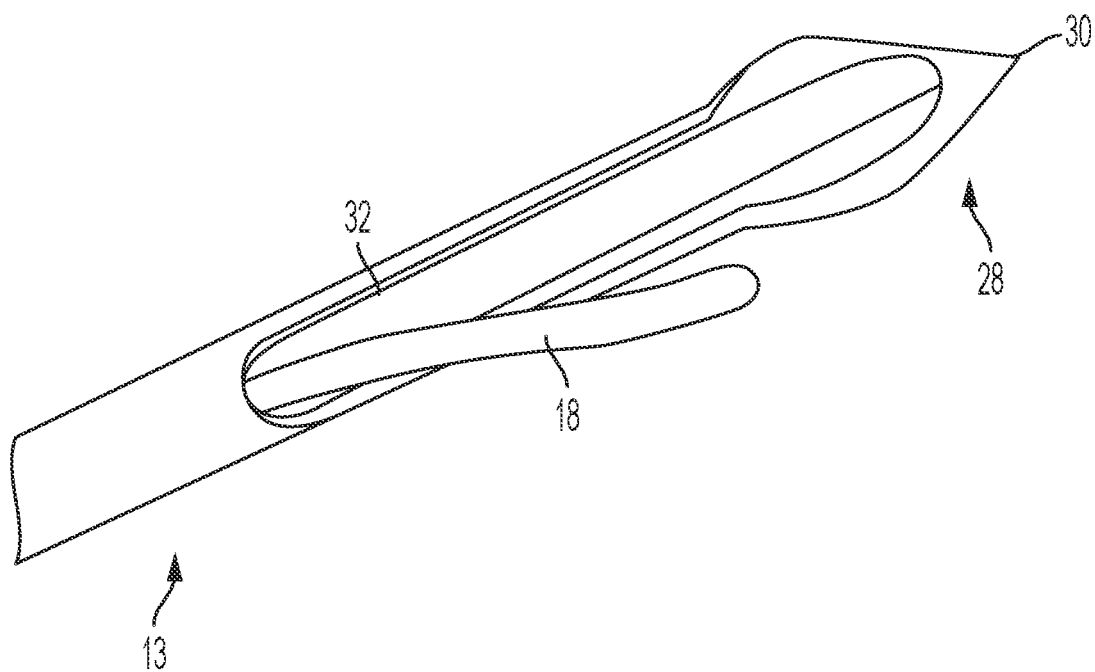
FIG. 2 is a top view schematic representation of a distal tip of the suture passer device, according to an embodiment.

Turning now to FIG. 2, there is shown a top view schematic representation of a distal tip 28 of the suture passer device 10, according to an embodiment. In the depicted embodiment, the curved distal tube portion 13 of the suture passer device 10 comprises a sharp distal tip 28. In FIG. 2, the distal tip 28 is tapered distally to a piercing point 30, which is used to pierce through a first (e.g., proximal) side of a tissue (not shown) or other object. The distal tip 28 extends proximally to a recessed portion 32 (i.e., longitudinal opening) in the distal end 16 of the curved distal tube portion 13. As shown in FIG. 2, the recessed portion 32 extends along a portion of the length of the distal tube portion 13. The internal arm 18 can be extended through the recessed portion 32 and retracted from the recessed portion 32 and into the distal tube portion 13 (or hollow tube 12).

Figure 3:
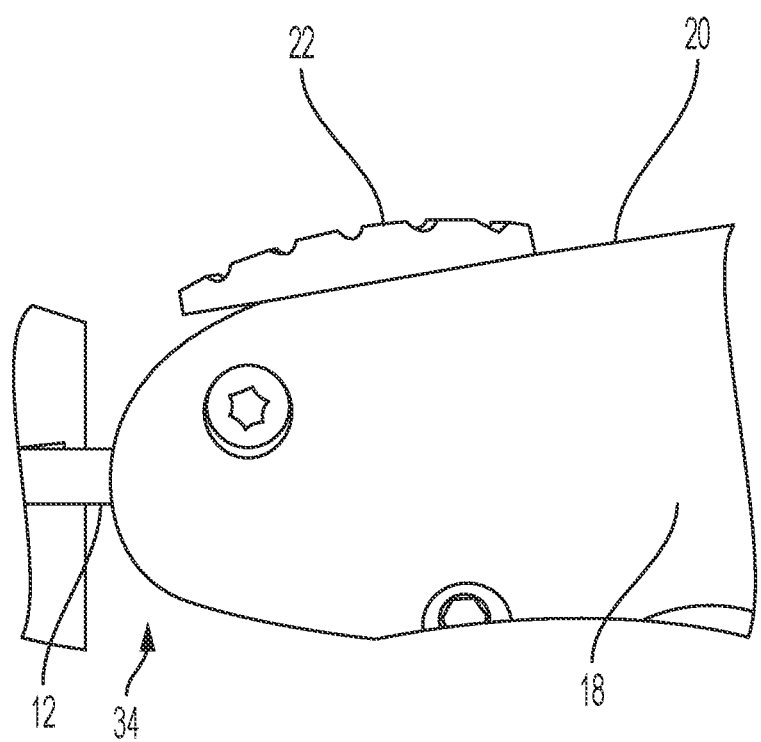
FIG. 3 is a side view schematic representation of an actuator of the suture passer device in a first position, according to an embodiment.

Referring now to FIGS. 3 and 4, there are shown side views schematic representations of the actuator 22 and the distal tube portion 13, respectively, of the suture passer device 10, according to an embodiment. As shown in FIG. 3, the actuator 22 can be a button, switch, or other protrusion that is slidable along the handle 20 (and can be slidable to multiple positions substantially along the longitudinal axis of the handle 20 toward the distal end and/or toward the proximal end to perform the actuation functionality described herein, by use of linear movement, the use of rotational movement per the use of internal gears moved by the linear movement of the actuator 22 (for example), or a combination of the two, as should be understood by a person of ordinary skill in the art in conjunction with a review of this disclosure). In a first configuration, the actuator 22 is in a first position along the handle 20 relative to a distal end 34 of the handle 20. When the actuator 22 is in the first position, the hook 26 and connected internal arm 18 are in the first configuration, extending out from the distal tube portion 13, as shown in FIG. 4. In the first configuration, the internal arm 18 (and the hook 26) extends at an angle from the distal tube portion 13 such that the hook 26 is spaced from the distal tube portion 13.

Figure 5:
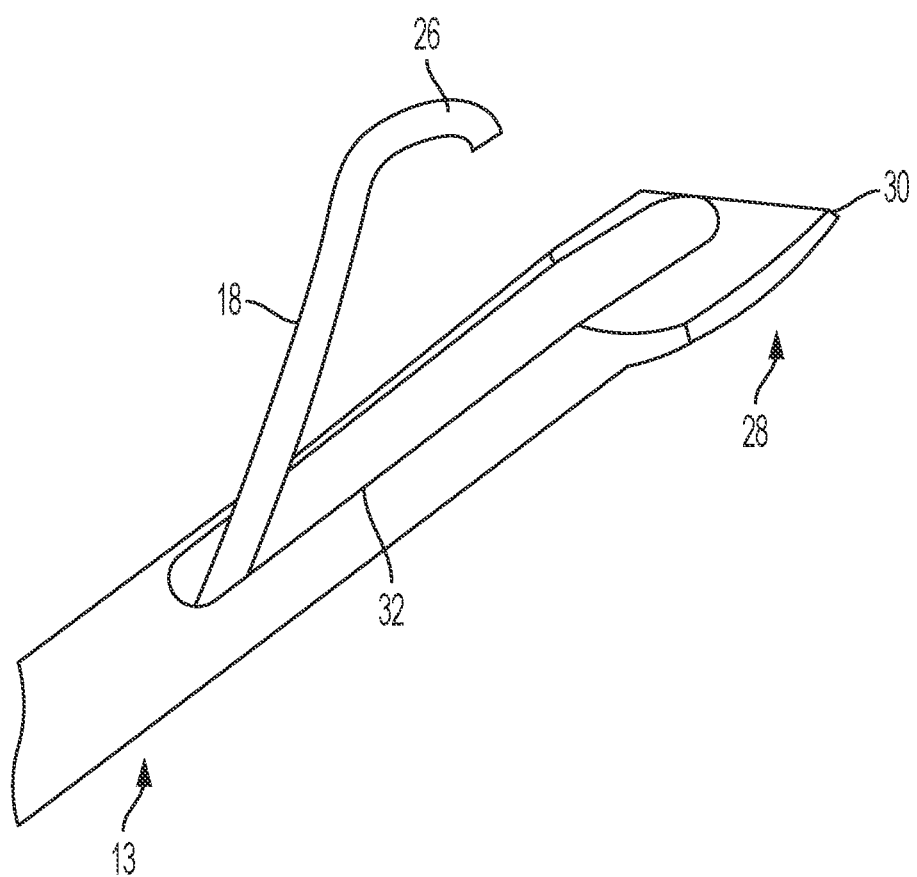
FIG. 5 is a side perspective view schematic representation of the distal tip of the suture passer device with the internal arm in the first configuration, according to an embodiment.

Turning now to FIG. 5, there is shown a side perspective view schematic representation of the distal tip 28 of the suture passer device 10 with the internal arm 18 in the first configuration, according to an embodiment. As shown, in the first configuration, the internal arm 18 (and the hook 26) protrudes at an angle out of the recessed portion 32. This creates space between the distal end 24 (or hook 26) of the internal arm 18 and the distal tube portion 13 to capture suture (not shown). In an embodiment, the suture is captured between the distal end 24 of the internal arm 18 and the distal tube portion 13 in a clip-like or clamp-like fashion. In an alternative embodiment, the suture is captured in the hook 26. The internal arm 18 can be biased to extend outward when not held in place by an internal surface (not shown) of the distal tube portion 13 when the internal arm 18 is in the second and third configurations.

Figure 6:
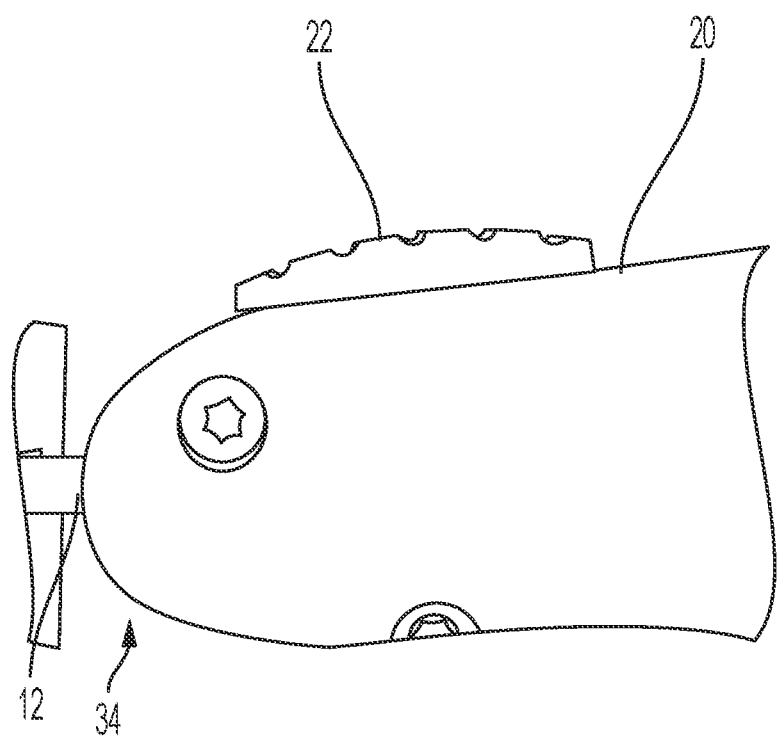
FIG. 6 is a side view schematic representation of the actuator of the suture passer device in a second position, according to an embodiment.
Figure 7:
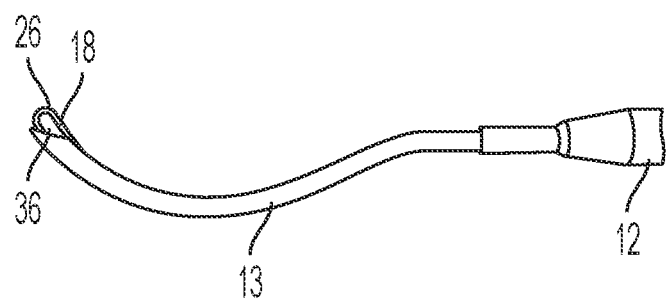
FIG. 7 is a side view schematic representation of the distal tube portion of the suture passer device in the second configuration, according to an embodiment.

Referring now to FIGS. 6 and 7, there are shown side views schematic representations of the actuator 22 and the distal tube portion 13, respectively, of the suture passer device 10, according to an embodiment. As shown in FIG. 6, in a second configuration, the actuator 22 is in a second position along the handle 20 relative to the distal end 34 of the handle 20. When the actuator 22 is moved from the first position to the second position, the hook 26 of the internal arm 18 rotates from the first configuration to the second configuration toward the distal tube portion 13 with the suture (not shown) maintained within the hook 26. When the actuator 22 is in the second position, the internal arm 18 is in the second configuration extending partially out from the distal tube portion 13, as shown in FIG. 7.

When the internal arm 18 is in the second configuration, there is minimal to no space between the hook 26 and the distal tip 28 of the distal tube portion 13. As shown in FIG. 7, the hook 26 may contact the distal tip 28 to create a closed aperture 36 through the hook 26, securing the suture (not shown) within the hook 26. The suture (not shown) is secured within the hook 26 such that the suture (not shown) cannot slip or fall out from the hook 26. Instead, the closed aperture 36 permits the suture (not shown) to slide within the closed aperture 36. Thus, the suture (not shown) can slide freely through the closed aperture 36 without falling entirely out from the hook 26.

Figure 9:
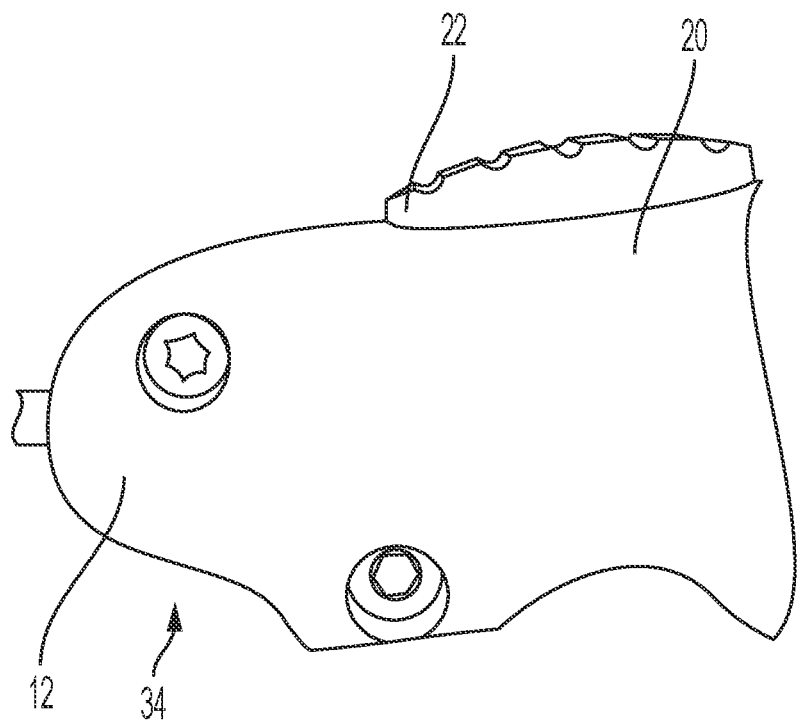
FIG. 9 is a side view schematic representation of the actuator of the suture passer in a third position, according to an embodiment.
Figure 10:
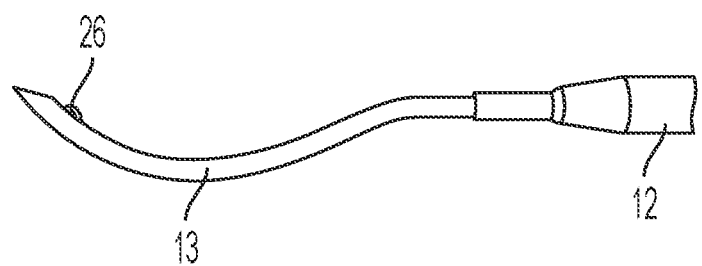
FIG. 10 is a side view schematic representation of the distal tube portion of the suture passer device in a third configuration, according to an embodiment.

Referring now to FIGS. 9-10 there are shown side views schematic representations of the actuator 22 and the distal tube portion 13, respectively, of the suture passer device 10, according to an embodiment. As shown in FIG. 9, in a third configuration, the actuator 22 is in a third position along the handle 20 relative to its distal end 34. In an embodiment, the actuator 22 is the most distal in the first position and most proximal in the third position, with the second position between the first and third positions. Other alternative relative positioning of the actuator 22 suitable for extending and retracting the internal arm 18 can be used. When the actuator 22 is moved from the second position to the third position, the hook 26 of the internal arm 18 is retracted from the second configuration to the third configuration within the distal tube portion 13.

Figure 8:
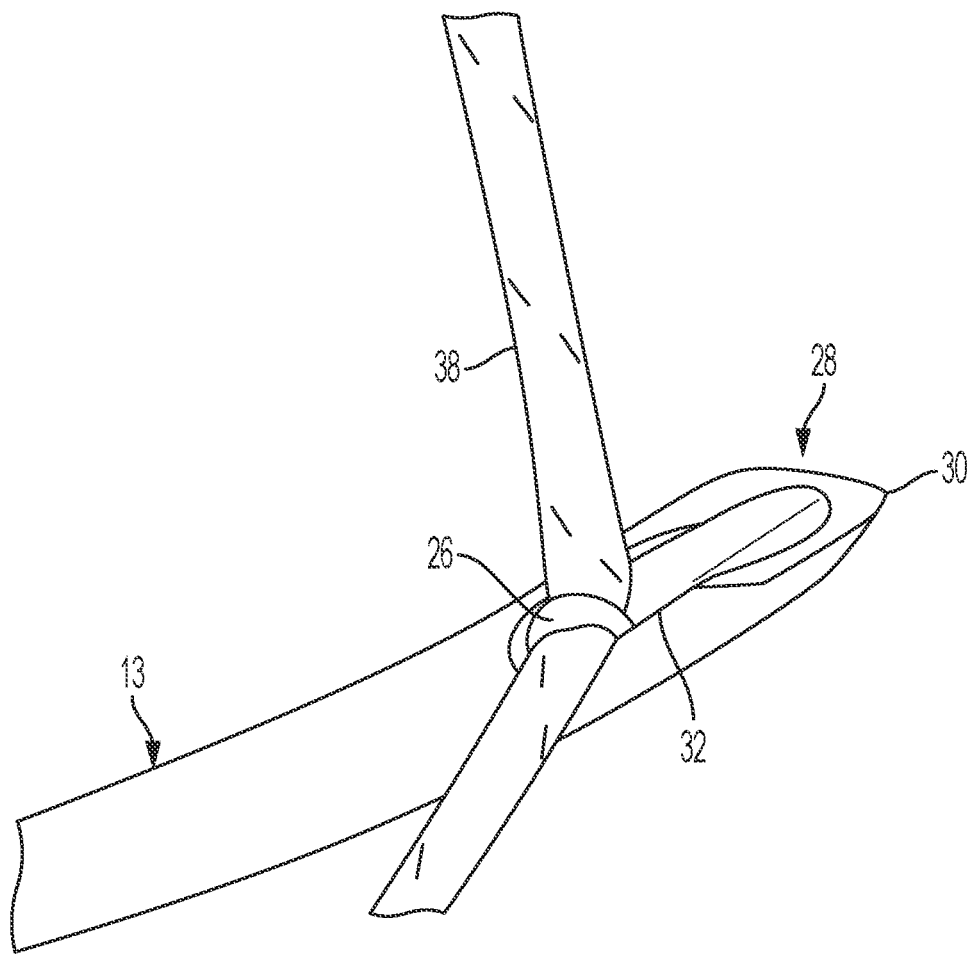
FIG. 8 is a top perspective view of the distal tip of the suture passer device between the second and third configurations with a passing suture, according to an embodiment.

When a length of suture 38 extends through the closed aperture 36, the suture 38 is pulled proximally into the distal tube portion 13, as shown in FIG. 8. In FIG. 8, the internal arm is between the second and third configurations and thus, the hook 26 having the secured suture 38 is almost entirely retracted into the distal tube portion 13. When the actuator 22 is in the third position, the internal arm 18 is in the third configuration wherein a majority of the hook 26 is retracted within the distal tube portion 13, as shown in FIG. 10. When the internal arm 18 is in the third configuration, the suture 38 extending through the closed aperture 36 in the hook 26 is pulled and locked within the distal tube portion 13.

In use, the actuator 22 is moved to the first position, causing the internal arm 18 to extend out from the distal tube portion 13 to achieve the first configuration. The suture 38 is then placed within the hook 26 (or between the straight distal end 24) and the distal tube portion 13. Thereafter, the actuator 22 is moved to the second position, causing the internal arm to rotate toward the distal tube portion 13 to achieve the second configuration (the actuator may also move proximally toward the proximal end of the device). In the embodiment wherein the distal tube portion 13 comprises a hook 26, the suture 38 is locked within the hook 26. The suture 38 is slidable within the hook 26 such that the user can advance the suture passer device 10 toward a first (e.g., proximal) side of the tissue without tensioning the suture 38.

Thereafter, the actuator 22 is moved to the third position, retracting the internal arm 18 proximally into the distal tube portion 13, achieving the third configuration. With the suture 38 secured in the distal tube portion 13 in the third configuration, the suture passer device 10 is advanced to pierce through the first side of the tissue (at a first passing location), not shown, with the piercing point 30 of the distal tip 28. Once the distal tube portion 13 extends from a second (e.g., distal) side of the tissue, the actuator 22 is advanced to the first position, causing the internal arm 18 to extend out from the distal tube portion 13, achieving the first configuration. In the first configuration, the suture 38 is released from the suture passer device 10.

With the suture 38 released on the second side of the tissue, the actuator 22 can be moved to the third position, retracting the internal arm 18 proximally into the distal tube portion 13 so that the internal arm 18 does not disturb or get caught on the surrounding tissue. The distal tube portion 13 is then pulled back through the tissue to the first side. To complete a stitch, the distal tube portion 13 (still in the third configuration) is passed through an adjacent second passing location on the tissue. Once on the second side of the tissue, the actuator 22 is moved to the first position, extending and rotating the internal arm 18 to the first configuration. The hook 26 (or distal end 24) of the internal arm 18 is used to catch the suture on the second side of the tissue, such as in the closed aperture 36 of the hook 26. The actuator 22 is then moved to the third position, securing the suture 38 within the distal tube portion 13, achieving the third configuration. Thereafter, the distal tube portion 13 is retracted from the tissue. This process can be repeated as necessary to complete any number of stitches, as should be understood by a person of ordinary skill in the art in conjunction with a review of this disclosure.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A suture passer device, comprising:
   a hollow tube having a proximal end and a distal tube portion extending to a distal end;
   a handle attached to the proximal end of the hollow tube;
   an actuator on the handle movable between a first position, a second position, and a third position;
   an internal arm within the distal tube portion and connected to the actuator, the internal arm comprising a distal end with a hook at the distal end and being movable between a first configuration, a second configuration and a third configuration;
   wherein when the actuator is in the first position, the internal arm extends out from the distal tube portion substantially along a first axis to a point immediately proximate to where the hook begins to curve and extends in a distal direction and at an angle from the distal tube portion in the first configuration; and
   wherein when the actuator is in the second position, the internal arm is retracted proximally further within the distal tube portion in the second configuration as compared to the first configuration, wherein when the internal arm is in the second configuration, the hook contacts the distal tube portion, forming a closed aperture through the hook; and
   wherein the distal tube portion consists of a single opening and has an overbite in a range of 3-5 mm over a midline of the hollow tube extending centrally through the distal tube portion, the distal tube portion further has a curved section that sweeps below the midline at a radius of curvature sufficient for the distal tube portion to be properly placed through a labrum during use;
   wherein when the actuator is in the first position, the internal arm extends through the single opening and the hook extends in the distal direction
   wherein when the actuator is in the third position and the distal tube portion is in the third configuration, wherein when the internal arm is in the third configuration, and wherein a majority of the hook is retracted within the distal tube portion, suture extending through the closed aperture in the hook is pulled and locked within the distal tube portion.

2. The suture passer device of claim 1, wherein the actuator is slidable proximally and distally between the first position and the second position relative to a distal end of the handle.

3. The suture passer device of claim 1, wherein the distal tube portion comprises a tapered distal tip with a piercing point.

4. The suture passer device of claim 1, further comprising a recess portion in the distal tube portion extending proximally from a tapered distal tip.

5. The suture passer device of claim 1, wherein the radius of curvature is about 9.3 millimeters.

* * * * *